United States Patent [19]
Saltzstein et al.

[11] Patent Number: 5,704,364
[45] Date of Patent: Jan. 6, 1998

[54] CONCURRENT MEDICAL PATIENT DATA AND VOICE COMMUNICATION METHOD AND APPARATUS

[75] Inventors: William E. Saltzstein, Amity; Damon J. Coffman, Portland; Scott M. Burkhart, Hillsboro, all of Oreg.

[73] Assignee: Instromedix, Inc., Hillsboro, Oreg.

[21] Appl. No.: 556,468

[22] Filed: Nov. 8, 1995

[51] Int. Cl.$^6$ .......................... A61B 5/04; A61B 5/0402
[52] U.S. Cl. .......................... 128/696; 128/904
[58] Field of Search .......................... 128/696, 904, 128/923; 364/413.07, 413.06

[56] References Cited

U.S. PATENT DOCUMENTS

| | | | |
|---|---|---|---|
| 3,886,314 | 5/1975 | Pori | 128/904 |
| 4,216,462 | 8/1980 | McGrath et al. | 128/904 |
| 4,494,553 | 1/1985 | Sciarra et al. | 128/903 |
| 4,784,162 | 11/1988 | Ricks et al. | 128/671 |
| 4,803,625 | 2/1989 | Fu et al. | 364/413.03 |
| 4,838,275 | 6/1989 | Lee | 128/904 |
| 4,933,873 | 6/1990 | Kaufman et al. | 364/413.02 |
| 4,945,477 | 7/1990 | Edwards | 607/5 |
| 5,007,429 | 4/1991 | Treatch et al. | 364/413.03 |
| 5,012,814 | 5/1991 | Mills et al. | 128/691 |
| 5,036,513 | 7/1991 | Greenblatt | 370/125 |
| 5,038,800 | 8/1991 | Oba | 128/696 |
| 5,142,484 | 8/1992 | Kaufman et al. | 128/630 |
| 5,216,596 | 6/1993 | Weinstein | 364/413.02 |
| 5,321,618 | 6/1994 | Gessman | 364/413.06 |
| 5,343,869 | 9/1994 | Pross et al. | 128/700 |
| 5,357,427 | 10/1994 | Langen et al. | 364/413.02 |
| 5,381,798 | 1/1995 | Burrows | 128/696 |
| 5,390,238 | 2/1995 | Kirk et al. | 128/904 |

(List continued on next page.)

FOREIGN PATENT DOCUMENTS 0 656 718 A   7/1995   European Pat. Off. ......... H04M 3/56

OTHER PUBLICATIONS

James E. McKee, Noel E. Evans and Frank J. Owens, A Simultaneous Full–Duplex Speech and Electrocardiogram Communication System, Proceedings of the Annual International Conference of the IEEE Engineering in Medicine and Biology Society, Baltimore, Nov. 3–6, 1994, vol. 16, pp. 902–903.

Stallings, William, *Data and Computer Communications*, 2nd Ed., Chapter 4–2, MacMillan Publishing Co., ©1988, pp. 103–113.

Segal et al., "Telephone Phonocardiography", *The American Journal of Medical Electronics*, Sep. 1964, pp. 189–190.

Primary Examiner—Marvin M. Lateef
Assistant Examiner—Carl H. Layno
Attorney, Agent, or Firm—Kolisch, Hartwell, Dickinson, McCormack & Heuser

[57] ABSTRACT

Method and apparatus for voice interaction between the service provider to the patient whose life signs, e.g. an electrocardiograph (ECG), concurrently are being monitored are described. Patient data and voice communication are conveyed on a single, or common, public switched telephone (PSTN) line. A life signs monitor at the patient site is connected to the patient and to a digital simultaneous voice and data (DSVD) device having the ability to digitize and compress the patient's voice and having the ability to decompress and analogize the physician's voice via a standard telephone. A modem modulates and demodulates transmitted and received data over the telephone line. At a remote monitoring site a second modem receives and transmits data over the same telephone line. The second modem is connected with a second DSVD device connected to a display- or printer-equipped receiving station for presentation in textual or graphic form to a remote service provider the patient data, e.g. in the form of an ECG trace. Thus, the service provider has the ability to overview patient life signs monitoring while in direct vocal communication with the patient, for instructing the patient or otherwise reassuring the patient of the proper use of the life signs monitor or diagnosing or prescribing in real-time response to what is gleaned from the monitoring.

14 Claims, 4 Drawing Sheets

U.S. PATENT DOCUMENTS

| | | | |
|---|---|---|---|
| 5,394,882 | 3/1995 | Mawhinney | 128/903 |
| 5,462,051 | 10/1995 | Oka et al. | 128/904 |
| 5,467,773 | 11/1995 | Bergelson et al. | 128/904 |
| 5,474,090 | 12/1995 | Begun et al. | 128/707 |
| 5,544,661 | 8/1996 | Davis et al. | 128/904 |
| 5,553,609 | 9/1996 | Chen et al. | 128/904 |
| 5,557,800 | 9/1996 | Kasimov et al. | 364/413.03 |

CONCURRENT MEDICAL PATIENT DATA AND VOICE COMMUNICATION METHOD AND APPARATUS

BACKGROUND OF THE INVENTION

The invention generally relates to remote medical patient monitoring. More particularly, it involves duplex patient monitoring communication over a single telephone line capable of concurrently carrying both medical practitioner voice and patient data.

Increasingly, medical patients are provided with portable, patient-proximate monitoring and control equipment that, in turn, is connected to a remote (typically centralized) healthcare provider, e.g. a physician, skilled technician or other service provider. Typically, patient vital sign data, e.g. an electrocardiograph (ECG) waveform, is digitized and transmitted over a phone line to the remote monitoring site for diagnostic, oversight and recording purposes. Conventionally, digital transmission protocols for use on voice-grade communications channels such as the public switched telephone network (PSTN) or cellular telephone network (CTN) use the entire available bandwidth for data transmission. This precludes the use of the phone for voice interaction between the physician and the patient.

To make the patient feel at ease, it is important to both the patient and the physician to interact the way they would during an office visit. Such interaction also provides the physician an opportunity to follow up any observations with questions to help diagnose the condition of the patient, as well as to offer reassurances and any needed instruction in the patient's use of the monitoring equipment. One solution to the problem would involve the use of two telephone lines, one for voice and one for data. Another solution presents itself with the advent of digital simultaneous voice and data (DSVD). It will be understood that "simultaneous" and "concurrent" are used interchangeably herein to describe concurrent voice and data communication.

DSVD uses digital signal processing and voice encoding to interleave voice data on a single communications channel. Current offerings are by AT&T (VoiceSpan™), Intel (ProShare™), U.S. Robotics, Inc. (Sportster VI™) and Multi-Tech Systems, Inc. (MultiTech®).

Current DSVD solutions are believed to be applicable to the above-described need for voice communication. On the other hand, medical grade monitoring over noisy phone lines at worst places the patient at risk (via degraded data integrity) and at best compromises vocal interaction (via degraded voice integrity). Special error detection and correction techniques therefore should be used when it is desired to use the PSTN for bi-directional, concurrent voice and data transmission in the medical patient monitoring field. Such error detection and/or correction is even more important when data is transmitted in a wireless conveyance such as over the CTN, which wireless communication is contemplated by the invention and is within the spirit and scope thereof.

It may be desirable also to include video data transmission over such a communication line. It is believed that the same methods used to divide the available bandwidth on a transmission channel could be "sliced" into more pieces, thereby creating a digital simultaneous voice, data and video (DSVDV) link. Depending upon the required refresh and resolution, it may be necessary to so communicate over the Integrated Services Digital Network (ISDN) or in accordance with the Asynchronous Transfer Mode (ATM). It is contemplated that current efforts to compress video for the multimedia market would be applicable to the invented method and apparatus, when it is desired to have one-way or two-way videoconferencing as a means for interaction between a patient and a service provider.

SUMMARY OF THE INVENTION

Thus, it is a principal object of the present invention to provide at least for concurrent digital medical patient data and voice communication over a single, duplex communication line.

It is another object of the invention to provide such digital and voice communication over the public switched telephone network (PSTN).

Still another object is to provide such communication in real time with minimum delay between the patient and physician.

Another important object of the invention is to provide such communication with high data and voice integrity.

Yet another object is to render the communication link's bandwidth automatically dynamically allocable to variable demand as between data and voice.

It is another object of the invention to provide also for the communication over such a line of digital video information in real time at a useful refresh rate.

Another object is to provide combined voice channels over the same single physical channel on which medical patient data is carried.

Still another object of the invention is to provide for the communication of medical patient data in any form, whether digital or analog, e.g. an audio signal representing the sound of the patient's heart, lung, stomach or other organ. In this alternative operational mode, an audio signal representing the sounds produced by a stethoscope, for example, may be transmitted to a remote site for overview by a medical service provider.

Thus, it will be understood that medical patient data is used in its broadest sense to include an analog signal suitable for transmission over a voice-grade telephone line. Briefly, the invention provides at least a voice monologue from the service provider to the patient whose life signs, e.g. ECG, are being monitored, and preferably provides a voice dialog therebetween, wherein both patient data and voice communication are conveyed on a single, or common, PSTN line. A life signs monitor at the patient site is connected to the patient and to a DSVD device having the ability to digitize and compress the patient's voice and having the ability to decompress and render in analog form the physician's voice via a standard telephone. Alternatively, auscultatory or ECG signals may be rendered in analog form, as by use of a stethoscope properly placed on the patient's body, for transmission as an analog, e.g. audio, signal rather than as a digital representation thereof.

A modem modulates and demodulates transmitted and received data over the telephone line. At a remote monitoring site a second modem receives and transmits data over the same telephone line. The second modem is connected with a second DSVD device connected to a display- or printer-equipped receiving station for presentation in textual or graphic form to a remote service provider the patient data, e.g. in the form of an ECG trace. Thus, the service provider has the ability to overview patient life signs monitored data while in direct vocal communication with the patient, for instructing the patient or otherwise reassuring the patient of the proper use of the life signs monitor or diagnosing or prescribing in real-time response to what is learned from the monitored data.

DETAILED DESCRIPTION OF THE PREFERRED EMBODIMENT

Figure 1:
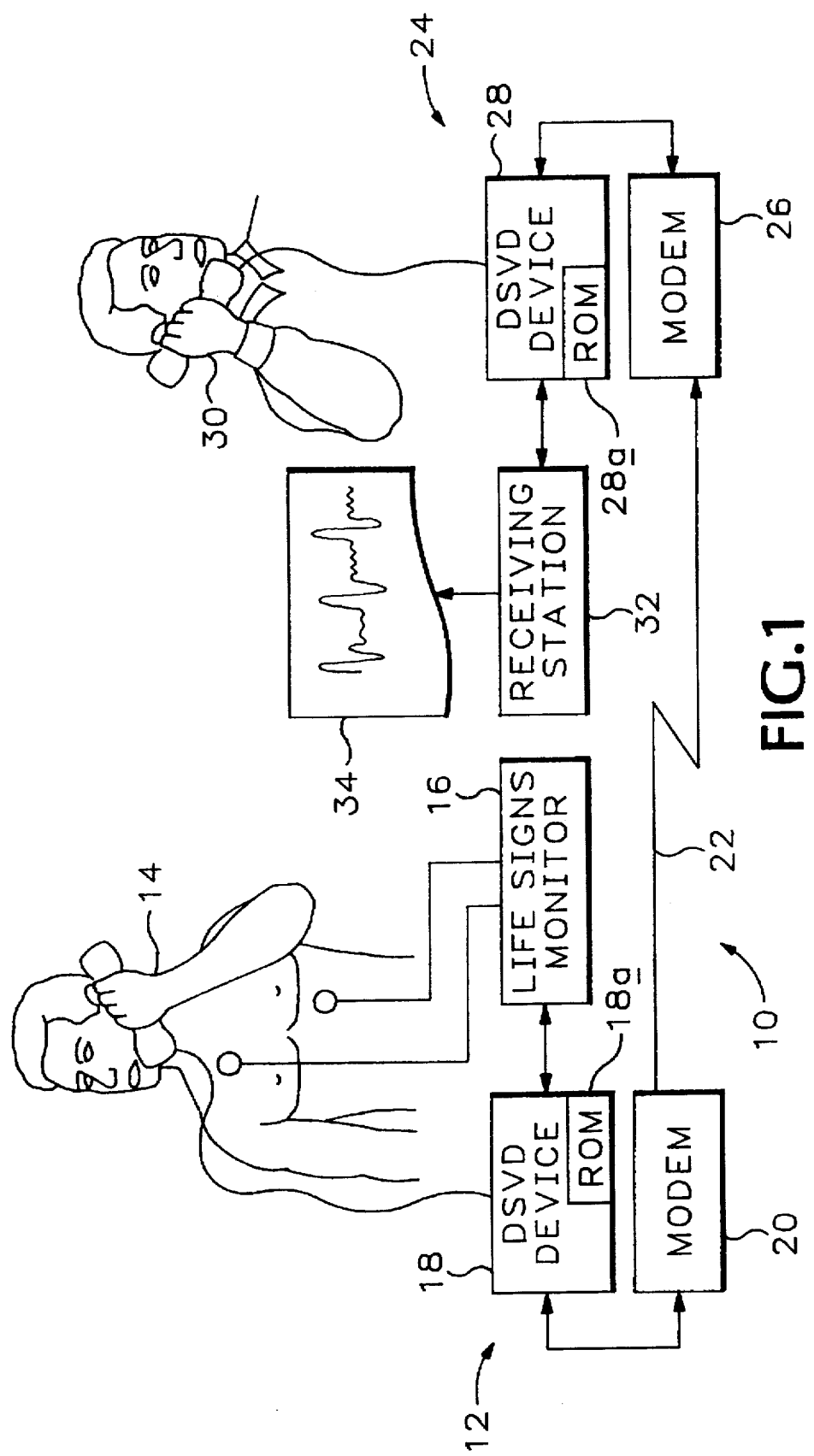
FIG. 1 is a system block diagram of the invented apparatus made in accordance with a preferred embodiment.

Referring first to FIG. 1, the invented apparatus made in accordance with its preferred embodiment is indicated generally at 10. At a patient site indicated generally at 12, a patient 14 is operatively connected to a life signs monitor 16, e.g. an electrode-equipped ECG monitor that senses the patient's skin potential variations, digitizes the signal and optionally records the digitized ECG waveform in an integral memory for immediate or deferred playback. It will be appreciated that life signs monitor 16 may be equipped to monitor any one or more desirable life signs, including vital signs such as 12-electrode ECG, pulse rate, blood pressure (bp), blood oxygen level (pulse oximetry), blood sugar level (glucometry), lung capacity (spirometry), etc., although only 2-electrode ECG monitoring is illustrated in FIG. 1. Life signs monitor 16 is operatively connected with a digital simultaneous voice and data (DSVD) device 18 that is capable of digitizing, compressing and time interleaving voice and data for transmission via a modem 20 over a single telephone line 22.

Preferably, DSVD device 18 supports duplex concurrent voice and data, thereby supporting at least a one-way instructional voice monologue from a remote physician, skilled technician or other service provider, and most preferably supporting a voice dialogue between patient 14 and the remote service provider. Importantly, such is rendered possible over a single, common telephone line, thereby obviating the need for more than one and making remote monitoring practical to at-home vital sign monitor patients. Such is the province of DSVD devices such as those available from AT&T (VoiceSpan™), Intel (ProShare™), U.S. Robotics, Inc. (Sportster Vi™) and Multi-Tech Systems, Inc. (MultiModem PCS®), all of which support concurrent digitized voice and data communication over the public switched telephone network (PSTN). Those skilled in the art will appreciate that any suitable DSVD device, whether it is so-called or whether it merely performs such functions as are described herein, is contemplated for use in invented apparatus 10, and is within the spirit and scope of the invention.

Preferably, in accordance with the invention, DSVD device 18 is specially equipped with error correction software or firmware 18a, preferably residing in its read and write memory (RAM) or read-only memory (ROM), that ensures the integrity of the patient data obtained from life signs monitor 16 or modem 20. Those of skill in the art will appreciate that such memory preferably may be any relatively high-density, low-cost volatile or non-volatile memory such as a block re-programmable, so-called "FLASH" memory device. Typically, modem 20 would provide some level of error correction, but it is important with patient data that the lowest possible bit error rate (BER) and frame error rate (FER) is maintained. Skilled persons will appreciate that the use of DSVD device 18 is only one currently preferred embodiment and that alternative embodiments nevertheless are within the spirit and scope of the invention. It will also be appreciated that the functions performed, in accordance with the preferred embodiment of the invention, in firmware residing within DSVD 18 alternatively may be performed by a central processor that is programmed to provide for the control of life signs monitor 16 and modem 20, as well as to perform the needed DSVD tasks, and that all such functions may be performed, within the spirit and scope of the invention, in software, firmware, hardware or any combination thereof.

One important aspect of the invention involves a patient data communication protocol that provides for automatic data validation by way of detection of transmission or reception errors. Preferably, the validation or verification technique includes serially communicating the patient data two or more times in succession, with identical patient data being accompanied by orthogonal error detection codes embedded within packet headers. An error that propagates through one error detection processor (however unlikely such may be) is rendered orders of magnitude less likely by the fact that the second error detection code is independent of the error methodology that permitted the error to propagate through the first processor. This invented technique is described herein as serial double fault tolerance. As will be seen, in accordance with the invention, if and only if data are error-free will they be transmitted and if and only if data are error-free upon their reception will they be permitted to affect patient diagnosis and treatment. Otherwise, the data will be flagged as being anomalous and no action will be indicated unless and until further valid medical patient data are transmitted and received without error. Such may be thought of as a zero-fault tolerance scheme.

Standards have been established for critical monitoring data communications. One such example is TÜV which stands for Technischer Überwachungsverein (which roughly translates into Technical Over-seeing Body), a German model for such communications applications that has been adopted by the European Community, familiarity with which is assumed. Generally, the TÜV standard requires that data representative of critical monitoring information such as patient vital signs be locally stored for transmission in at least two memory locations for local comparison and verification purposes. Those of skill in the art will appreciate, however, that the would-be identical data in the various locations in memory may be corrupted and yet may be in agreement with one another such that one or more data errors exists but is detected.

Alternatively or additionally to the preferred patient data error correction technique described above, patient data integrity may be assured by a service provider, who may perform patient data oversight while in voice communication with the patient. For example, a physician or skilled technician or other service provider who notes an apparently anomalous ECG waveform, very simply and without additional cost in accordance with the present invention, may instruct or request that the patient or patient device re-transmit the dubious data that has been recorded by the patient equipment. The human factor thus provides a significant advantage over conventional life signs monitoring that relies solely on communication electronics and/or protocols to ensure data integrity. It is unlikely that a temporary adverse condition of a telephone line, e.g. a momentary carrier disruption, would occur twice in short succession. Thus, a subsequent transmission of patient data that was corrupted by such a condition of the communication conveyance typically would result in a successful transmission of accurate patient data, yet in real-time (albeit slightly delayed) response to what might be a life-threatening condition for the monitored patient.

Referring still to FIG. 1, it may be seen that telephone line 22 is connected a at a remote monitoring site, indicated generally at 24, to a second modem 26 which may be identical to modem 20. A second DSVD device 28 operatively connected to modem 26 performs essentially the same functions as DSVD device 18 at patient site 12. Second DSVD device 28 also preferably is equipped with specialized error correction firmware residing in a ROM 28a integral with second DSVD device 28. DSVD device 28 includes a voice port for at least one-way, and preferably two-way, voice communication by a physician, skilled technician or other service provider 30. Operatively connected with DSVD device 28 is a receiving station 32 capable of producing a display or printout 34 of tabulated data, ECG traces or other textual or graphic illustrations of the monitored life signs of patient 14, e.g. the ECG waveform shown in FIG. 1. Thus, in accordance with the invention, service provider 30 is able not only to overview a patient's monitored life signs, but also to vocally interact with the patient during such overview.

Those of skill in the art will appreciate that DSVD device 18 and modem 20 may be integral with one another, and may be packaged as a stand alone unit or as a board that may be installed in a personal computer (PC) or workstation. Similarly, DSVD device 28 and modem 26 may be integral with one another, and may be similarly packaged. As mentioned above, it is contemplated also that the functions of DSVD 18 may be performed instead by an application program executing on a PC having no DSVD per se but having the required signal processing capabilities. It will also be appreciated that life signs monitor 16 may be integral with DSVD device 18 or may be a board that may be installed in such a PC or workstation located at patient site 12. Similarly, it will be appreciated that receiving station 32 may be equipped with an integral display or printer for producing display or printout 34, and that receiving station 32 may be integral with DSVD device 18 or may be a board that may be installed in such a PC or workstation located at monitoring site 24. Life signs monitor 16 alternatively may be worn by patient 14 as a neck-worn pendant or wrist-worn watch, and it may wirelessly communicate patient data to DSVD device 18. Those skilled in the art will appreciate that DSVD devices 18, 28 may have integral microphones and speakers to provide patient 14 and service provider 30, respectively, with a hands-free voice communication alternative to a standard telephone handset. Of course, as discussed herein, such a handset may be replaced or augmented with a stethoscope forming a part of a telephone or having a built-in microphone or other transducer capable of convening audio vibrations to an electrical signal. All such alternative configurations and their functional equivalents are within the spirit and scope of the invention.

Those of skill in the art now may appreciate that the invented method and apparatus promote better voice communication between physician and patient. Most homes have only one telephone line, and previously there has been no possibility of concurrent voice communication between a physician and a patient who is being transtelephonically monitored. With the present invention, voice communication is possible during a monitoring session. For example, a physician might inquire of the patient during vital signs monitoring of the patient's general health, whether the patient has been taking prescribed medications, regarding the patient's diet and regularity, e.g. urinary or bowel movement, etc. Such information is vital to an assessment of the patient's well-being, and may greatly assist the physician in interpreting the monitored vital signs. It also tends to place the patient at greater ease during what for some is a stressful monitoring session. Thus, more full service remote diagnosis and treatment of patients is possible by use of the invented method and apparatus.

Figure 2:
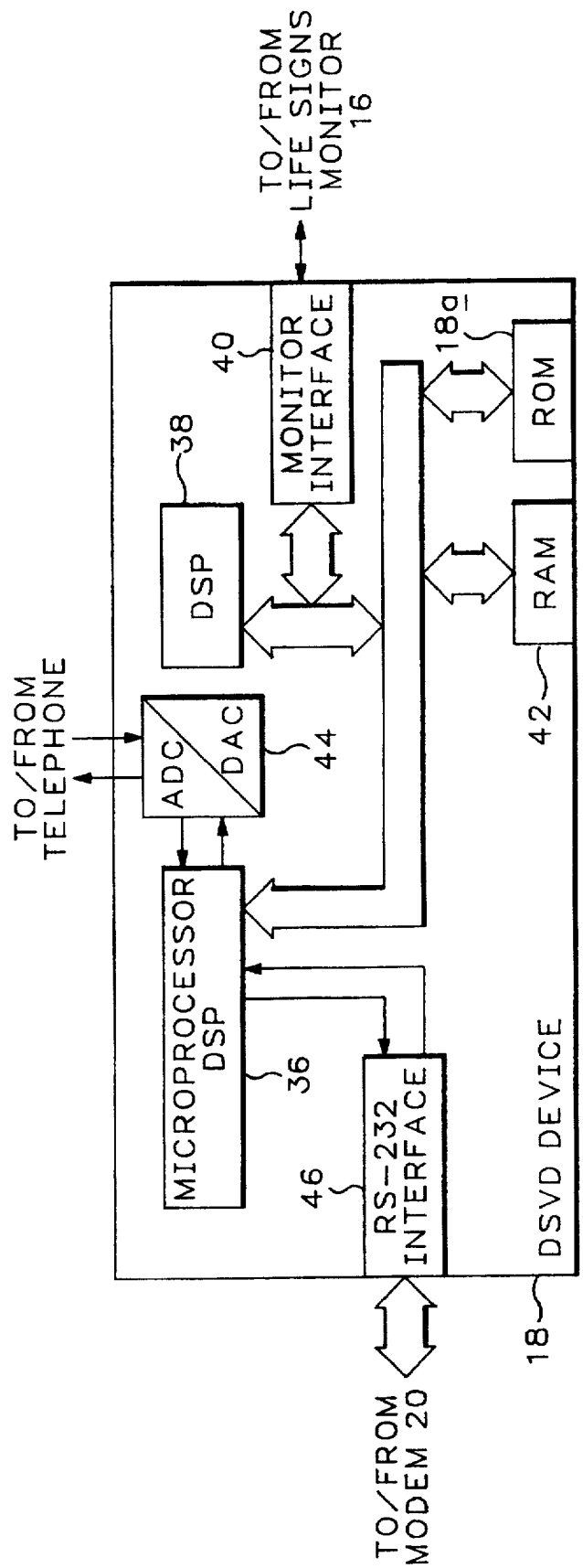
FIG. 2 is a detailed schematic diagram of one of the digital simultaneous voice and data (DSVD) devices shown in FIG. 1.

Turning now to FIG. 2, DSVD device 18 will be described by reference to a detailed schematic diagram. (Those skilled in the art will appreciate that DSVD device 28 would be substantially identically described and illustrated, with RS-232 and digital interface connections instead to modem 26 and to receiving station 32.) In addition to ROM 18a, DSVD device 18 preferably includes a microprocessor (μPROCESSOR) 36, a digital signal processor (DSP) 38, a life signs monitor interface 40 connectable, in turn, to life signs monitor 16 (not shown in FIG. 2, but shown in FIG. 1) and a read-and-write memory (RAM) 42 all connected to a common data/address bus as indicated by the broad lines. Microprocessor 36 also has an input/output (I/O) port connected to an analog-to-digital converter (ADC) and digital-to-analog converter (DAC) 44 connectable, in turn, to a telephone (not shown in FIG. 2, but shown in FIG. 1). Finally, microprocessor 36 has an I/O port connected to an RS-232 or similar, preferably EIA-standard, interface 46 connectable, in turn, to modem 20 (not shown in FIG. 2, but shown in FIG. 1).

Figure 3:
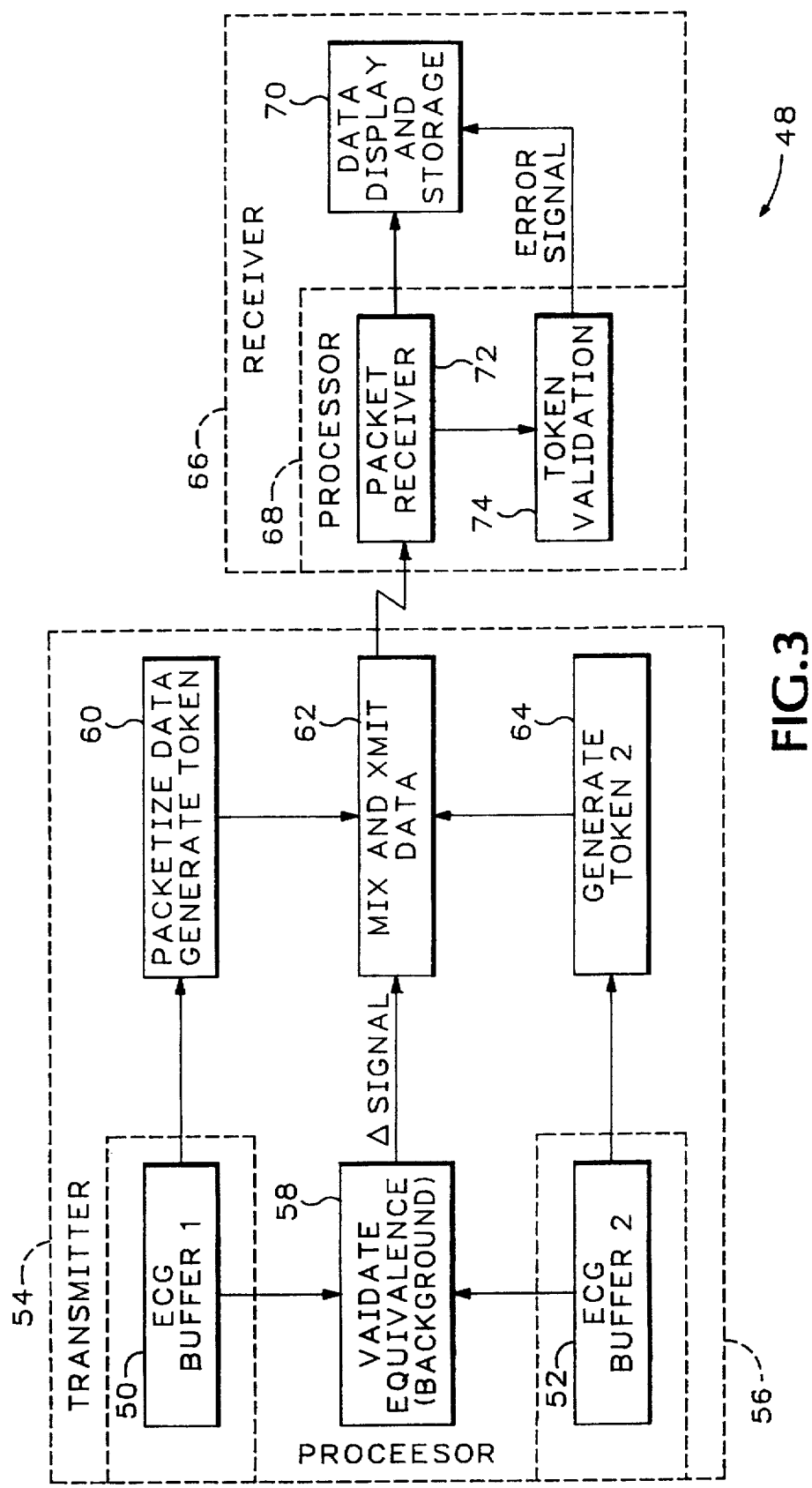
FIG. 3 is a schematic block and data flow diagram illustrating the invented medical data verification method and apparatus of the invention.

Referring now to FIG. 3, invented apparatus for telecommunicated medical data verification is indicated at 48. In accordance with this feature of the invention, medical data error rates are reduced to near-zero by the use of what will be referred to herein as serial double fault error-prevention technique. By way of background, it will be appreciated that current serial data communication has achieved a level of integrity whereby corrupted data reception already is highly improbable. Typically utilized techniques involve cyclic redundancy checking (CRC) of transmitted data by appending to the transmitted data packet a unique code that is a boolean combination of the data that is transmitted, whereby a receiver performs a checksumming by similar combination to detect corrupted data bits within the received data stream. If uncorrectable data errors are detected by the receiver, typically the communication protocol requires retransmission of the data packet until an uncorrupted, or at least a correctable, data packet is received. Of course, such retransmissions, or retries, result in degraded data throughput, which depending upon the level of degradation can seriously impact applications which are dependent upon the timely arrival of uncorrupted data at the receiver.

Communication channels that introduce chaotic noise to the communication of life critical data have not been adequately addressed by conventional data error detection/correction techniques and protocols. The invented serial double fault technique may be used in applications where hardware, software or firmware (or a combination thereof) acquires critical data, and renders potentially life-sustaining and life-threatening decisions based thereon. The invented technique borrows somewhat from mathematical or logical redundancy theory, and is akin to getting a second medical opinion before proceeding with an extensive or intensive therapeutic or surgical procedure. In a preferred embodiment of the invention, dual processors monitor critical life data and produce—by independent techniques—a key or token derived therefrom and then compare their results prior to any data-based decision making. Only if the two independent processors agree that critical life data is uncorrupted is a life-critical action initiated by the processors on the basis of the data. Importantly, the independence of the processors that derive the key or token is ensured by the way in which they are designed, preferably by independent design teams in a "clean room" environment. Absent agreement between the two independent processors, i.e. without unanimity of 'opinion' regarding a patient prescription, professional intervention is invoked as by annunciating to a competent medical practitioner the inability of the processors to agree on a prescribed course of action.

In accordance with a preferred embodiment of the invention, a key or token is embedded in each logical data packet that is communicated. A separate data packet containing a complementary key is transmitted synchronously or asynchronously relative to each of the first packets. The receiving station validates the complementary of the two keys via execution of an independent algorithm. This provides a first level of reliability in life critical data communication, all but eliminating random line noise data corruption.

A second level of reliability is ensured by the way in which keys or tokens are created. Each of two keys—a primary and a complementary key—is created by a different technique or algorithm from data residing at the transmitter in different data stores or memory buffers. By generating the keys by diverse methods from diverse sources, the probability of transmitter-internal data corruption is reduced nearly to zero. And by this redundant and independent data verification technique, key-creation process integrity is exported to the receiver.

Communication error correction protocols, however, only validate the data stream from point 20 to point 26 (see FIG. 1). Those skilled in the art will appreciate that not only has conventional transmission error detection been made more robust, but the concept of detection and correction has been extended to the very root of data generation, by the invented method and apparatus. Thus, the requirements for internal data consistency by regulatory bodies such as the FDA and TÜV have been extended to cover the entire data creation-transmission-reception link in vital medical data. Thus, the users of medical patient data, e.g. doctor, nurse, caregiver, are guaranteed the accuracy of the vital patient data just as they would obtain were they in immediate proximity to the patient and patient monitoring system. As a result, the invented method and apparatus meet the most rigorous error correction and safety standards. Those skilled in the art will appreciate that this concept may be extended, without any loss of generality, to cover other items of safety concern such as power monitoring, infusion pump failure, etc.

The invented apparatus will now be described in another way, by reference to FIG. 3. Invented apparatus 48 may be seen from FIG. 3 to include in an illustrative but not limiting ECG monitoring application two independent ECG data buffers 50, 52 within an ECG data monitor/transmitter station 54. It will be appreciated that, in accordance with invention, buffers 50, 52 may be implemented as any one or more memory devices, whether volatile or non-volative, e.g. magnetic or electronic such as read-and-write memory (RAM), charge-coupled device (CCD), 'flash' memory, etc. Monitor/transmitter station 54 also preferably includes a processor 56, e.g. an appropriately programmed microprocessor executing instructions out of read-only memory (ROM) or a functional equivalent. Processor 56 preferably includes a comparator/validator 58 for contrasting the independent data from buffers 50, 52 to produce a difference signal ("ΔSIGNAL") if any, which is fed to the input of a mixer/packet transmitter. Those of skill in the art will appreciate that the illustrated difference signal, when present, is used by the mixer/packet transmitter to correct transmitter-internal errors prior to the transmission of packetized data over a communication line such as a telephone line.

Buffer 50 is operatively connected with a data packetizer/token generator 60 the packetized/token-appended output of which is fed to a mixer/packet transmitter 62. Buffer 52 is operatively connected with a second data packetizer/token generator 64 the output of which is connected to another input of mixer/packet transmitter 66. The error-corrected output of mixer/packet transmitter 62 is communicated preferably bit-serially over the conventionally schematically illustrated communication line to a remote receiver indicated generally at 66. Preferably, receiver 66 includes a processor 68 such as a ROM-instructed microprocessor and a data display and/or storage and/or hardcopy device 70.

Processor 68 preferably includes a packet receiver 72 and a token validation device 74, the latter of which produces an error signal, if any. It will be appreciated that device 70, within the spirit and scope of the invention, may take any suitable form. For example, it may be a video display terminal (VDT) capable of imaging the monitored data in textual, graphical or any other suitable form. Alternatively, it may be a simple strip chart recorder for graphic ECG waveform hardcopy production or a line printer for textual ECG waveform data hardcopy production. Alternatively, it may be simply a storage device such as any suitable volatile or non-volatile memory device such as tape, disc, CCD, RAM, etc. It will be understood that one prescribed function performed by device 70 is to utilize the error signal produced by token validation device 74 and to correct any discovered errors in the ECG data that is received by packet receiver 72.

Briefly summarizing the invented error detection and avoidance method, dual tokens or checksum are generated from independently stored data buffers and the tokens are compared to ensure their agreement. A single token in agreement with both independently generated tokens then is appended to a single copy of the data packets indicated by the token comparisons to have been in agreement, and the agreeable data packet and its appended agreeable token are transmitted from patient site 12. At a remote overview site, the data packet and its appended token are received and the token is validated before any patient condition is diagnosed or any remedial action is taken. Only is the received token indicates that the received medical patient data are valid would the medical service provider take a remedial action in response to received medical patient data. Of course, it will be appreciated that, most often, medical patient data will be transmitted and received error-free and remedial action taken as indicated. Thus, the invented error detection and avoidance technique gives the highest level of assurance that the right thing is being done for the patient at all times.

The invented apparatus now will be understood to provide concurrent voice and medical data communication over a common link. As illustrated in FIGS. 1 and 3, invented apparatus 48 preferably comprises a life signs monitor 16 at a patient site 12 responsive to a medical patient 14 for producing medical data—e.g. ECG, pulse, bp, blood oxygen or sugar levels, lung capacity, etc.—representative of the patient's life signs; a memory device such as one or more of buffers 50, 52 for storing such medical data; a transmitter 54 for transmitting such medical data from the memory device via a communication line 22; a remote receiver 66 at an overview site 24, receiver 66 being coupled with communication line 22 for receiving such medical data for presentation to a medical service provider 30; and a telephone link such as that illustrated in FIG. 1 and described herein for at least one-way voice communication from service provider 130 to patient 14, with the telephone link utilizing common communication line 22 for such voice communication and such data transmission.

Preferably, the telephone link provides two-way voice communication between service provider 30 and patient 14, although it will be appreciated that perhaps the more important communication is from service provider 30 to patient 14. As described herein, such voice communication from service provider 30 to patient 14 may include instructing patient 14 on the use of monitor 16 or may be of a more general advice or reassurance nature. As described herein, such responsive voice communication from patient 14 to service provider 30 may include status or observation information regarding monitor 16 or may be of a more general nature, e.g. confirmation that patient 14 is taking his or her prescribed medications or information regarding the patient's health. In accordance with invention, it is possible to provide for two-way, patient site-to-service provider site, voice communication, in addition to patient data transmission from patient site to service provider site over a single, common telephone line that typically is available anywhere within the PSTN.

In accordance with the preferred embodiment of the invention, the memory device includes at least two medical data buffers 50, 52, and transmitter 54 includes a comparator or comparator/validator 58 for generating a difference signal upon detection of a difference between corresponding data within the two buffers. Also in accordance with the preferred embodiment of the invention, transmitter 54 further includes for each of the preferably two medical data buffers 50, 52 a buffered data packetizer and a token generator capable of producing a token symbolizing such packetized buffered medical data, e.g. packetizer/generators 60, 64. Further in accordance with the preferred embodiment of the invention, transmitter 54 further includes a mixer 62 responsive to each of the tokens produced by packetizer/generators 60, 64 and to the difference signal to produce a transmit data packet representing more highly correlated, and thus accurate, medical patient data.

Those of skill will appreciate that, with redundant buffering of what should be identical medical patient data, with comparison thereof and generation of a signal representing any difference therebetween, with using such a difference signal to mix independently generated data packet tokens to produce a single data packet and an appended validation token—as illustrated in FIG. 3 and as described herein—it is possible in accordance with invention to ensure the very highest possible data integrity for transmission to a remote physician site over a standard voice-grade telephone line.

Further in accordance with the invented apparatus, preferably receiver 66 includes a transmit data packet receiver 72 and a token validator 74 capable of determining whether the transmit data packet received by packet receiver 72 is valid, with token validator 74 producing an error signal for use by receiver 66 to determine whether the data is 'believed' by the independent transmitter and receiver processors to be accurate, in which case the patient data is presented in tabular, graphic or alternative form on a presentation device—e.g. a VDT, printer, strip-chart or magnetic medium recorder, facsimile machine, personal computer (PC), personal digital assistant (PDA) or any other useful recording, output or presentation device—or whether instead the patient data is 'believed' to be suspect in which case the service provider is so informed. Those of skill will appreciate that one or more of such alternative recording, output and presentation devices may be selected at the remote physician site under the automatic switching control of a patient data server device such as a dedicated PC.

Figure 4:
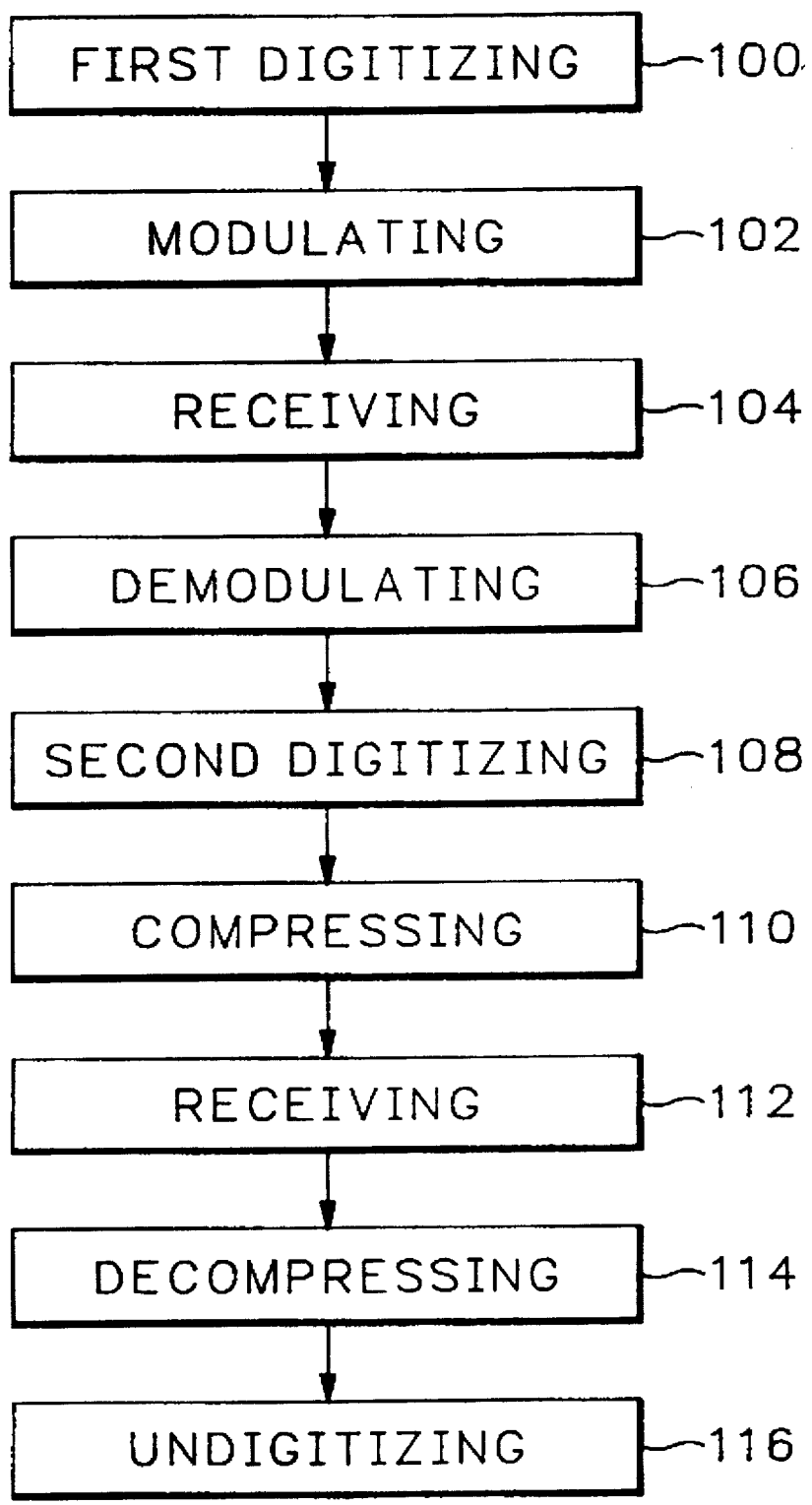
FIG. 4 is a flowchart that illustrates the preferred method of the invention.

Referring next to FIG. 4, the preferred method of the invention now is described. The invented medical patient monitoring method will be understood to be for concurrently communicating physician voice and patient data over a single telephone line. Preferably, the method comprises the following steps: 1) at 100 FIRST DIGITIZING the patient data for transtelephonic communication to a remote monitoring site; 2) at 102 MODULATING a single-line carrier with such digitized data in such manner that the data modulation is substantially inaudible to the physician and to the patient and in such manner as to permit sufficient remnant bandwidth for compressed voice communication; 3) at 104 and 106, respectively, RECEIVING and DEMODULATING such digitized data at such remote monitoring site for physician overview of the patient data; 4) concurrently with FIRST DIGITIZING step 100, MODULATING step 102 and RECEIVING and DEMODULATING steps 104, 106, SECOND DIGITIZING at 108 and COMPRESSING at 110 the physician voice, at such monitoring site, in such manner as to fit within such remnant bandwidth.

The preferred method of the invention further preferably comprises 5) at 112 and 114, respectively, RECEIVING and DECOMPRESSINC; and 6) UNDIGITIZING at 116 such digitized and compressed physician voice at patient site 12, thereby permitting concurrent communication of patient data to monitoring site 24 and of physician voice to patient site 12. Those skilled in the art will appreciate that, by performing SECOND DIGITIZING and COMPRESSING steps 108, 110 concurrently with FIRST DIGITIZING, MODULATING, RECEIVING and DEMODULATING steps 100, 102, 104, 106 both patient medical data and physician voice signal may be transmitted (albeit in different directions) within the limited voice bandwidth of a PSTN telephone line, in accordance with invention. Those of skill in the arts also will appreciate that such in accordance with the preferred method of the invention may be performed by apparatus 10 or 48, as illustrated in FIGS. 1 or 3, wherein processors 56 and 68 are suitably programmed to effect such invented method.

Preferably the invented method is adaptive automatically to allocate the single-line bandwidth between patient data and physician voice, wherein a higher patient data communication rate occurs responsive to and concurrent with a lower physician voice communication demand. Such adaptive line bandwidth allocation preferably is accomplished by use of a DSVD device such as DSVD device 28 having a suitably programmed ROM 28a (or, alternatively, suitable hardware or software or any combination thereof), as shown in FIG. 1. By the use of such invented method, those of skill in the art will appreciate that the physician voice, responsive to such overview of the patient data, provides feedback to the patient regarding the patient monitoring, as described above by way of the use model. A typical patient such as patient 14 is equipped with patient life signs monitoring equipment or simply life signs monitor 16 such that the physician voice, responsive to such overview of the patient data, provides instruction to the patient regarding use of such equipment. It will be appreciated by skilled persons that such instruction might include requesting that patient site 12 perform a re-transmission of previously overviewed patient data, as in the case where it is determined by receiver 66 (see FIG. 3) via the illustrated error signal has received corrupted medical patient data.

The method preferably further comprises providing for concurrent duplex voice communication concurrent with the patient data communication, wherein patient data, physician voice and patient voice are communicated over the single telephone line such as that illustrated at 22 in FIG. 1 and described herein as typically being a part of the ubiquitous PSTN. Typical of such voice communications, the physician voice, responsive to such overview of the patient data, provides feedback to the patient regarding the patient monitoring. Also typical of such voice communications, the patient voice, responsive thereto, provides acknowledgement to the physician regarding the feedback therefrom. Any and all such one-way or two-way voice communications between patient 14 and service provider 30 are contemplated, and are within the spirit and scope of the invention.

Also in accordance with the invented method, at patient site 12 the patient data is appended with an error correcting code such as either or both tokens produced by packetizer/generators 60, 64 to produce error correction-coded patient data. In such a case, at the monitoring site such error correction-coded patient data is checked, at least, as by use of token validator 74 and the illustrated error signal produced thereby, and corrected as necessary. Thus, the preferred method of the invention further includes patient data error detection including transmission and reception of a validation code that is appended to such digitized data, wherein if a data error is detected then no patient-remedial action is taken.

Those of skill in the art will appreciate that, alternatively or additionally to the illustrated token generation and validation, conventional methods may provide for medical patient data error detection and correction. For example, the error correcting code may take the form of a cyclic redundancy coding (CRC) scheme, as is conventional and as such will not be further described herein. In these and other contexts, the preferred method of the invention may further comprises patient data error correction including re-transmission of previously overviewed patient data via physician voice instruction to the patient site upon detection by the physician of apparently anomalous patient data. Any such medical patient data error avoidance, detection and correction techniques is contemplated and is believed to be within the spirit and scope of the invention.

Thus, those skilled in the art will appreciate that, by common link, single telephone line, single-line carrier, single-line bandwidth and the like is meant conventional PSTN or equivalent conveyance for carrying a single, full-duplex telephone call in which two-way voice communication for years has been provided by local and long-distance telephone companies, whereby separate essentially simplex or half-duplex lines and their attendant cost are obviated. Typically, such PSTN conveyances have been characterized by a single, twisted pair of conductors connected via a dedicated line to a local switching network, wherein two speakers' analog voices signals are picked up by a microphone within a handset, are amplified and transmitted bi-directionally to a remote handset's speaker over a relatively narrow audible frequency range of approximately 1,000–4,000 Hz or a bandwidth of approximately 3,000 Hz.

Thus, by single, duplex communication link or line very simply generally is meant the functional equivalent of a single pair of conductors representing a voice and ground wire pair having a characteristic impedance and other electrical parameters that permit coherent, two-way, analog voice communication between two arbitrarily distant telephones. It will be understood that such, within the spirit and scope of the invention, may take an equivalent wireless form such as a single telephone line used in cellular, satellite, fiber-optic or other communications media.

The invention thus may be understood to represent a significant improvement over conventional medical patient monitoring techniques and equipment that provide only for the simplex trans-telephonic communication of patient data. The improvement may be summarized briefly as providing for medical patient data error avoidance, detection and/or correction in a PSTN telephone link-based system that provides not only patient data monitoring but also one-way or two-way concurrent voice communication over a common voice-grade line.

Accordingly, while a preferred embodiment of the invention has been described herein, and preferred methods associated therewith, it is appreciated that modifications are possible that are within the scope of the invention.

It is claimed and desired to secure by letters patent:

1. A medical patient monitoring method for concurrently communicating physician voice and patient data over a single telephone line, the method comprising:

first digitizing the patient data for transtelephonic communication to a remote monitoring site;

modulating a single-line carrier with such digitized data in such manner that the data modulation is substantially inaudible to the physician and to the patient and to permit sufficient remnant bandwidth for compressed voice communication;

receiving and demodulating such digitized data at such remote monitoring site for physician overview of the patient data;

automatically allocating the single-line bandwidth between patient data and physician voice, wherein a higher patient data communication rate occurs responsive to and concurrent with a lower physician voice communication demand;

concurrently with said first digitizing, said modulating and said receiving and demodulating, providing for voice communication concurrent with the patient data communication by digitizing and compressing the physician voice, at such remote monitoring site, to fit within such remnant bandwidth; and receiving and decompressing and undigitizing such digitized and compressed physician voice at the patient site, thereby permitting concurrent communication of patient data to such remote monitoring site and of physician voice to such patient site.

2. The method of claim 1, wherein the physician voice, responsive to such overview of the patient data, provides feedback to the patient regarding the patient monitoring.

3. The method of claim 2 in which the patient is equipped with patient monitoring equipment, wherein the physician voice, responsive to such overview of the patient data, provides instruction to the patient regarding use of such equipment.

4. The method of claim 3, wherein such instruction includes requesting that the patient site perform a re-transmission of previously overviewed patient data.

5. The method of claim 1 which further comprises providing for concurrent duplex voice communication concurrent with the patient data communication, wherein patient data, physician voice and patient voice are communicated over the single telephone line.

6. The method of claim 5, wherein the physician voice, responsive to such overview of the patient data, provides feedback to the patient regarding the patient monitoring and wherein the patient voice, responsive thereto, provides acknowledgement to the physician regarding the feedback therefrom.

7. A medical patient monitoring method for concurrently communicating physician voice and patient data over a single telephone line, the method comprising:

first digitizing the patient data for transtelephonic communication to a remote monitoring site;

modulating a single-line carrier with such digitized data in such manner that the data modulation is substantially inaudible to the physician and to the patient and to permit sufficient remnant bandwidth for compressed voice communication;

receiving and demodulating such digitized data at such remote monitoring site for physician overview of the patient data;

selectively correcting errors in the patient data by transmission and reception of a validation code that is appended to such digitized data, wherein if a data error is detected then no patient-remedial action is taken;

concurrently with said first digitizing, said modulating and said receiving and demodulating, providing for voice communication concurrent with the patient data communication by digitizing and compressing the physician voice, at such remote monitoring site, to fit within such remnant bandwidth; and receiving and decompressing and undigitizing such digitized and compressed physician voice at the patient site, thereby permitting concurrent communication of patient data to such remote monitoring site and of physician voice to such patient site.

8. A medical patient monitoring method for concurrently communicating physician voice and patient data over a single telephone line, the method comprising:

first digitizing the patient data for transtelephonic communication to a remote monitoring site;

modulating a single-line carrier with such digitized data in such manner that the data modulation is substantially inaudible to the physician and to the patient and to permit sufficient remnant bandwidth for compressed voice communication;

receiving and demodulating such digitized data at such remote monitoring site for physician overview of the patient data;

selectively correcting errors in the patient data by re-transmission of previously overviewed patient data via physician voice instruction to the patient site upon detection by the physician of apparently anomalous patient data;

concurrently with said first digitizing, said modulating and said receiving and demodulating, providing for voice communication concurrent with the patient data communication by digitizing and compressing the physician voice, at such remote monitoring site, to fit within such remnant bandwidth; and receiving and decompressing and undigitizing such digitized and compressed physician voice at the patient site, thereby permitting concurrent communication of patient data to such remote monitoring site and of physician voice to such patient site.

9. Apparatus for providing concurrent voice and medical data communications over a common link, the apparatus comprising:

a life signs monitor at a patient site responsive to a medical patient for producing medical data;

a memory device for storing such medical data, wherein said memory device includes at least two medical data buffers;

a communications line;

a telephone link for at least one-way voice communications between a service provider and the medical patient, said telephone link utilizing said communication line for such voice communication;

a converter for digitizing such medical data and such voice communication;

a transmitter coupled to the communication line for simultaneously transmitting such digitized medical data and voice communication, and wherein said transmitter includes a comparator for generating a difference signal indicative of substantially error free data upon detection of a difference between corresponding data within said two buffers; and a remote receiver at an overview site, said receiver being coupled with the communication line for receiving such digitized medical data and such voice communication for presentation to a medical service provider.

10. The apparatus of claim 9, wherein said transmitter further includes for each of said medical data buffers a buffered data packetizer and a token generator capable of producing a token symbolizing such packetized buffered medical data, and wherein said transmitter further includes a mixer responsive to each of said tokens and to said difference signal to produce a transmit data packet representing more highly correlated medical patient data.

11. The apparatus of claim 10, wherein said receiver includes a transmit data packet receiver and a token validator capable of determining whether said transmit data packet is valid, said token validator producing an error signal for use by said receiver to determine whether the transmitted data packet is valid.

12. Apparatus for providing concurrent voice and medical data communication over a common link, the apparatus comprising:

a life signs monitor at a patient site responsive to a medical patient for producing medical data;

a memory device for storing such medical data, wherein the memory device includes at least two medical data buffers;

a communications line;

a transmitter coupled to the communications line for transmitting such medical data from the memory device, wherein the transmitter includes a comparator for generating a difference signal indicative of substantially error free data upon detection of a difference between corresponding data within said two buffers;

a remote receiver at an overview site, said receiver being coupled with the communication line for receiving such medical data for presentation to a medical service provider; and a telephone link for at least one-way voice communication from the service provider and the patient, said telephone link utilizing said communication line for such voice communication.

13. The apparatus of claim 12, wherein said transmitter further includes for each of said medical data buffers a buffered data packetizer and a token generator capable of producing a token symbolizing such packetized buffered medical data, and wherein said transmitter further includes a mixer responsive to each of said tokens and to said difference signal to produce a transmit data packet representing more highly correlated medical patient data.

14. The apparatus of claim 13, wherein said receiver includes a transmit data packet receiver and a token validator capable of determining whether said transmit data packet is valid, said token validator producing an error signal for use by said receiver to determine whether the transmitted data packet is valid.

* * * * *